United States Patent [19]  [11] 3,963,577
Shinkarenko et al.  [45] June 15, 1976

[54] LYTIC ENZYME AND METHOD OF PREPARING SAME

[76] Inventors: Ljubov Nikolaevna Shinkarenko, ulitsa Komsomolskaya, 64/66, kv. 4; Julia Semenovna Babenko, ulitsa Gogolya, 27a, kv. 35; Evgeny Fedorovich Grigoriev, ulitsa Darvina, 40, kv. 1, all of Dnepropetrovsk, U.S.S.R.

[22] Filed: Sept. 16, 1974

[21] Appl. No.: 506,746

[30] Foreign Application Priority Data

Sept. 28, 1973 U.S.S.R. .............................. 1962088

[52] U.S. Cl. .................................. 195/62; 195/65; 195/66 R
[51] Int. Cl.² .......................................... C12K 1/00
[58] Field of Search ....................... 195/62, 65, 66 R

[56] References Cited
UNITED STATES PATENTS
3,716,452  2/1973  Kitamura et al. ...................... 195/62
3,868,303  2/1975  Tsumura et al. ................... 195/65 X

OTHER PUBLICATIONS

Chemical Abstracts, vol. 79, 3850u (1973).

Chemical Abstracts, vol. 80, 58356p (1974).

*Primary Examiner*—A. Louis Monacell
*Assistant Examiner*—Robert J. Warden
*Attorney, Agent, or Firm*—Steinberg & Blake

[57]  ABSTRACT

A method for preparing a lytic enzyme comprising growing Actimomyces recifensis var. *lyticus* 2435 in a nutrient medium, containing sources of nitrogen, carbon and mineral salts at a temperature of 25°–28°C. for 3–5 days, separating Actinomyces recifensis var. *lyticus* 2435 from the culture medium and then isolating the lytic enzyme from the culture medium.

7 Claims, No Drawings

LYTIC ENZYME AND METHOD OF PREPARING SAME

This invention relates to a new lytic enzyme and to a method of preparing the same.

The proposed new lytic enzyme can be used for processing protein-vitamin concentrates to improve their nutritive properties and to ensure better utilization in the animal body; for more complete isolation of biologically active substances with predominantly intra-cell localization (some antibiotics, enzymes, amino acids, vitamins, nucleic acids); for control of some pathogenic microbes; for preparing enzymatic lysates of microbeal mass (wastes of various microbiological processes) for their utilization in the manufacture of nutrient media; for cultivation of microorganisms; for preparing valuable protein concentrates and fortification of food with these concentrates. The new lytic enzyme can also be used in medicine to treat superficial affections of various etiology.

According to the invention, the new lytic enzyme is prepared by cultivating strain Actinomyces recifensis var. lyticus 2435 on a nutrient medium containing sources of nitrogen, carbon, and mineral salts, at a temperature of 25° – 28°C for three or five days. The mycelium is then separated and the end product is isolated from the culture fluid.

Strain Actinomyces recifensis var. lyticus 2435 is deposited in the Museum of Cultures of the Microbiology Chair at the State University of Dniepropetrovsk. This strain is isolated from loamy soil by cultivation on selective agar medium containing mineral salts NaCl and $K_2HPO_4$, Staphylococcus aureus cells as the source of nitrogen and carbon, and has the following morphological nd physiological characteristics: diameter of aerial mycelium 0.7 – 0.9 m; sporangiophores are short, non-spiral, arranged in bundles; spores are oblong, the membrane is smooth; the aerial mycelium is greyish-green, the substrate mycelium is darker; propagation on Czapek medium is good, the colonies are greyish, the surface is velvety; propagation on Hause I medium is good, the colonies are velvety, the aerial mycelium is greyish-green, the substrate mycelium is greyish-brown; no brown substance is formed; in depth cultivation, mycelium forms balls of entangled threads with a small number of branches; medium cloudiness disappears, and yellowish brown colour develops; the culture relates to aerobic, and requires intense aeration in the process of cultivation; it can propagate at pH within a wide range (from 4 to 10) without losing its ability to synthesize enzymes; propagates at a temperature of 10° – 45°C; quickly and effectively thickens gelatin; peptonizes milk; poorly hydrolyzes starch; reduces nitrates; tyrosinase is negative; poorly propagates on cellular tissues; assimilates well almost all sugars, but their presence in the medium reduces the synthesis of lytic enzymes; it is a weak antagonist, and manifests a moderate antibiotic activity with respect to separate types of gram-positive bacteria and yeast, and does not inhibit the growth of gram-negative forms.

It is recommended that the process of cultivation should be carried out on nutrient media having the following composition: (in per cent by weight): soya bean flour 0.3, glucose 0.5, $K_2HPO_4$ 0.01, $NH_4NO_3$ 0.1, microelements: $CaCl_2$ 0.11, $MnCl_2$ 0.0012, $MgCl_2$ 0.047, $FeSO_4$ 0.00152, $CuSO_4$ 0.000016, $ZnSO_4$ 0.000017, and water to make 100.

The process of cultivation should preferably be carried out at a temperature of 25° – 28°C, with aeration, for three days.

It is recommended that before inoculation of the medium, an inducer of synthesis of lytic enzymes, namely, cells of cultures Staphyloccoccus aureus, Micrococcus glutamicus, Bacillus subtilis, Salmonella galliarum or Saccharomyces cerevisiae should be introduced into the culture medium. A suspension of the inducer, containing 0.85 – 1 mg of protein per ml, is introduced into the medium at a ratio of 1:10 with respect to the nutrient medium.

The end product should preferably be isolated by saturation of the culture fluid with ammonium sulphate, to 40 – 60 per cent by weight, with subsequent desalting and drying. The obtained lytic enzyme produced by the strain Actinomyces recifensis var. lyticus 2435 has the following characteristics: it is stable within a wide range of pH (from 4 to 9); the optimum pH is 4.5 – 5.0; it retains its potency at a temperature of 4°C for a long time and is inactivated with heating to 60°C for 15 minutes; the action of the enzyme is inhibited by Cu, Zn, Mn, Fe, and cystine; it is activated with Ca, Mg and Co; ethylenediaminetetraacetic acid (EDTA) does not inhibit the enzyme activity; the enzyme destroys to 80 – 100 per cent of killed and live cells of the microorganisms pertaining to the genera Staphylococcus, Diplococcus, Micrococcus, Escherichiae, Brucellae, Corynebacterium, Arthrobacter, Salomonella, Bacillus, Vibrio, Mycobacterium, some yeasts — Saccharomyces, Torulopais, Candida; it can produce lysis in chlorella cells.

The proposed lytic enzyme possesses a much wider spectrum of action as compared with the known enzymes. Its action extends not only onto many gram-positive microorganisms, but it also destroys effectively cell walls of gram-negative bacteria and yeast cells.

Known bacteriolytic enzymes of actinomycetes are characterized by a limited spectrum of action which only extends to some types of gram-positive microorganisms.

Actinomyces griseus forms two staphylolytic enzymes; the spectrum of the action is narrow and specific. Actinomyces globisporus in active only with respect to gram-positive microorganisms Streptococcus, Lactobacillus, Bacillus, and is incapable of destroying gram-negative microorganisms and yeast. The great advantage of the proposed lytic enzyme is that it can destroy the membrane of chlorella by 30 per cent, and thus increases its nutritive value.

The proposed method can be realized as follows.

The fermentation medium is inoculated with the mother culture Actinomyces recifensis var. lyticus 2435 grown on Czapek medium with constant stirring (in flasks on reciprocating shakers) for five days. The inoculation is carried out with blocks of 7–10-day-old culture grown on Czapek medium and having the following morphological and physiological characteristics: diameter of aerial mycelium is 0.7 – 0.9 m, sporangiophores are short, non-spiral, almost straight, slightly wavy in young species, arranged in bundles; the spores are oblong, slightly elongated, the membrane is smooth.

With most media, the aerial mycelium is greyish-green, sometimes pale-green the colonies are; coloured rather than the media.

With Czapek medium the growth is intense, the colonies are 2 – 4 mm in diameter, the colour of the colonies is greyish-green, the mergins are plain, the surface is velvety, sometimes slightly wavy, with crater-like depressed centres.

With starch-ammonia medium the growth is good, the colonies are greyish-green, sometimes with a yellowish tint.

With Hause I medium the growth is good, the surface of the colonies is velvety, the colour of the aerial mycelium is greyish green, of the substrate mycelium greyish-brown.

With Hause II medium the growth is good, the aerial mycelium is greyish-green, the substrate mycelium is red-brown. No brown substance is formed.

With beef peptone agar medium the growth is normal, the sporulation is retarded, the colonies are sometimes asporogenic, almost non-coloured, of pale-grey colour.

With yeast agar and maltose, the growth is ample, the colonies are brown-green. The aerial mycelium is greyish-yellow.

On the surface of liquid media it propagates as a tubercular, thick, greyish-white film, and colours the media yellowish-brown of variable intensity.

With depth cultivation, the mycelium is in the form of balls of entangled threads with a small number of branches.

Cloudiness of the medium during cultivation disappears and a yellow-brown colour develops.

Physiological and biochemical properties:

The culture is an aerobic one, and requires intense aeration during cultivation.

It can grow and propagate within a wide range of pH of the medium, viz., from 4.0 to 10, without losing its ability to synthese enzymes. The optimum pH for the synthesis of enzymes is 7 – 8.

Grows at temperatures from 10° to 45°C, the optimum temperature being 27° – 28°C.

It thins gelatin quickly and intensively; peptonizes milk. It poorly hydrolyzes starch, reduces nitrates, and does not produce tyrosinase. Poorly grows on cellular tissue. It assimilates practically all sugars but their presence in the medium, at increased concentrations in particular, decreases the synthesis of lytic enzymes.

It is a weak antagonist, displays a moderate antibiotic potency with respect to some gram-positive bacteria and yeast, does not inhibit the growth of gram-negative forms.

The inoculum is grown at a temperature of 25°–28°C with continuous bubbling of sterile air through the medium. The process is continued for 3–5 days. As the culture is propagating, daily samples are taken to test for sterility and the biological potency.

On the termination of the growth cycle, the culture fluid is separated from mycelium and unused remnants of the nutrient medium is centrifuging or filtering.

The lytic activity is determined in the culture fluid, and if it attains the level of 60 per cent, the enzyme is isolated there from.

The lytic activity is determined as follows.

A suspension of live cells of *Staphylococcus aureus* is used as a rule for determining the lytic activity. To 2 ml of the suspension of living cells of the test culture are added 2 ml of the culture fluid or the fermented solution, and the initial optical density of the obtained suspension is measured on an absorptiometer with a yellow filter (the optical density should be 1.0 – 1.5). The suspension is then thermostatted at a temperature of 37°C for 60 – 210 minutes. Cloudiness that develops, is recorded at 15-minute intervals.

The degree of lysis of the test culture is determined from the following formula $$\frac{a_1 - a_2}{a_1} 100,$$

where
$a_1$ is the optical density of the starting suspension,
$a_2$ is the density of the suspension in $t$ time, that is, the density which is built up by the undissolved cells.

The lytic degree and its rate are used to determine the activity of the obtained lytic enzyme.

The lytic enzyme should preferably be isolated by saturing the culture fluid with ammonium sulphate to 40 – 60 per cent. The saturated salt solution is allowed to stand for 16 – 18 hours in a refrigerator to precipitate proteins which are then separated by centrifuging or filtration in vacuum.

The precipitated proteins are washed several times with cold acetone, dried slightly to remove acetone, and dissolved in a buffer for dialysis. The dialysis is carried out against a solvent for 18 – 24 hours, the dialysate is then dried lyophilically. The obtained lytic enzyme has an original nature, it is not an actinomycetic protease, nor does it show amylolytic activity. The proposed new lytic enzyme has the following characteristics: stability within a wide range of pH of the medium — from 4 to 9; the optimum pH is from 4 to 4.5; active at a temperature of 25° – 50°C; the optimum temperature 37°C; can be stored for lengthy periods at +4°C; inactivated with heating to 60°C for fifteen minutes; the enzyme action is inhibited by Zn, Cu, Mn, Fe, and cystine; Ca, Mg, and Co activate its action; EDTA does not produce any effect on the lytic activity.

The lytic enzyme is characterized by the following spectrum of its action, as illustrated in the Table which follows hereinafter:

Table

| Microorganisms | Lysis depth, in % | |
|---|---|---|
| | killed cells | living cells |
| 1. Staphylococcus aureus | 100 | 100 |
| 2. Diplococcus sp. | 100 | 100 |
| 3. Micrococcus glutamicus | 100 | 90 |
| 1 | 2 | 3 |
| 4. Micrococcus pyogenes | 67 | 2.3 |
| 5. Micrococcus lysodeiklicus | 42 | 2.5 |
| 6. Sarcina lufea | 18.0 | 6.0 |
| 7. Bacillus anthracaides | 100 | 100 |
| 8. Bacillus mycaides | 100 | 80 |
| 9. Bacillus subtilis | 100 | 70 |
| 10. Bacillus megaterium | 70 | 16 |
| 11. Escherichia coli 5026 | 100 | 90 |
| 12. Escherichia coli 0-111 | 100 | 85 |
| 13. Escherichia coli 5031 | 100 | 80 |
| 14. Escherichia coli 3050 | 100 | 60 |
| 15. Escherichia coli 0-55 | 90 | 30 |
| 16. Salmonella gallinarum | 93 | 20 |
| 17. Corynebacterium sp. | 100 | 97 |
| 18. Mycobacterium B-5 | 100 | 85 |
| 19. Vibrio sp. | 90 | 75 |
| 20. Zigomyces bailii | 90 | 75 |
| 21. Saccharomyces cerevisiae | 95 | 63 |
| 22. Candida guilliermondii | 90 | 60 |
| 23. williopnis saturnis | 80 | 55 |
| 24. Torulopsis utilis | 75 | 40 |
| 25. Candida tropicalis | 54 | 20 |
| 26. Chlorella | — | 29 |

EXAMPLE 1

A nutrient medium containing (in per cent by weight) soya bean flour 0.3, glucose 0.5, $K_2HPO_4$ 0.01, $NH_4NO_3$ 0.1, $CaCl_2$ 0.11, $MnCl_2$ 0.0012, $MgCl_2$ 0.047, $FeSO_4$ 0.00152, $CuSO_4$ 0.000016, $ZnSO_4$ 0.000017, having the pH 7.5 – 7.9 (before sterilization in an autoclave) is inoculated with a 5-day-old mother culture of *Actinomyces recifensis* var. lyticus 2435 grown on Czapek liquid medium with constant shaking. The inoculum is added in the quantity of 8 – 10 per cent.

The cultivation is continued for three days at a temperature of 25° – 28°C with continuous stirring and bubbling with sterile air.

In three days of the incubation the lytic activity of the culture medium attains its maximum.

| Incubation period | Protein content of culture fluid, in mg/liter | Activity Lytic activity, % in 60 min | Proteolytic activity, PU/ml |
|---|---|---|---|
| 74 hours | 5 | 94 | 0.34 |

The culture medium is centrifuged (6,000 rpm) for 10 – 15 minutes to remove mycelium and unused nutrient medium. The centrifuging and all further operations are performed at lowered temperatures.

Then, ammonium sulphate is added in small portions to attain 40 per cent saturation. The salt solution is allowed to stand in a refrigerator for 16 – 18 hours to precipitate protein. The protein is then separated from the culture fluid by centrifuging at 6,000 rpm for 20 minutes.

The protein precipitate is washed with cold acetone, dried slightly in a succinate buffer of 0.01 M, at pH 4.5 (at the ratio of 1:10 with respect to the starting volume of the culture fluid). The insoluble precipitate is removed by centrifuging at 4 – 5 thousand r.p.m. for ten minutes.

The protein solution is dialyzed against a solvent through a semipermeable membrane for 18 – 24 hours. The dialysis is carried out in a refrigerator at a temperature of +4°C.

The dialysate is dried lyophilically to prepare 5 – 6 g of dry lytic enzyme per litre of the culture fluid.

EXAMPLE 2

By a procedure similar to that described in Example 1, the culture medium is inoculated by *Actinomyces recifensis* var. lyticus 2435. Before inoculating the medium, a suspension of cell culture of inducer *Staphylococcus aureus* is added to it. The suspension contains 0.85 – 1 mg/ml of protein. The suspension is added in the quantity of 100 ml per 1000 ml of the nutrient medium.

The inoculation and all other operations are performed in the same manner as described for Example 1.

After a 3-day incubation, the lytic activity of the culture fluid, with respect to some live test-cultures, is as follows.

| Inducer | Lytic activity, in % for 60 min. | | |
|---|---|---|---|
| | St. aureus with respect to: | Bacillus subtilis | Sacch. cerevisiae |
| Staphylococcus aureus | 54 | 66 | 20 |

The lytic enzyme is isolated as in Example 1.

EXAMPLE 3

*Micrococcus glutamicus* inducer cells are added to the nutrient medium before inoculation as described in Example 2. The procedure is the same as described in Example 1. Protein content of the inducer suspension is 0.85 – 1 mg/ml. The inducer is added in the ratio of 1:10 with respect to the nutrient medium.

The lytic activity with respect to living test cultures on the third day of incubation is as follows:

| Inducer | Lytic activity (in % for 60 minutes) | | |
|---|---|---|---|
| | St.aureus | Bac.subtilis | Sacch.cerevisiae |
| Micrococcus glutamicus | 56 | 99 | 37 |

The lytic enzyme is isolated as in Example 1.

EXAMPLE 4

The procedure is the same as described in Example 1. Cells of inducer *Bacillus subtilis* are added into the nutrient medium before inoculation. All other operations are the same as described in Example 1.

The lytic activity of the culture fluid with respect to living test-cultures on the third day of incubation is as follows:

| Inducer | Lytic activity (in % for 60 minutes) with respect to cultures: | | |
|---|---|---|---|
| | St.aureus | Bac.subtilis | Sacch.cerevisiae |
| Bac.subtilis | 75 | 62 | 60 |

The lytic enzyme is isolated as described in Example 1.

EXAMPLE 5

The procedure is the same as described in Example 1. A suspension of inducer *Salmonella gallinarum* is introduced into the nutrient medium before inoculation. All other operations are the same as in Example 1. The lytic activity of the culture fluid with respect to live test-cultures is as follows:

| Inducer | Lytic activity (in % for 60 minutes) with respect to cultures | | |
|---|---|---|---|
| | St.aureus | Bac.subtilis | Sacch.cerevisiae |
| Salmonella gallinarum | 60 | 80 | 28 |

The lytic enzyme is isolated as in Example 1.

EXAMPLE 6

The process is carried out by a procedure described in EXAMPLE 1. Cells of inducer *Saccharamoces cerevisiae* are introduced to the nutrient medium before inoculation. The incubation and all other operations are carried out as described in Example 1.

The lytic activity of the culture fluid with respect to live test cultures is as follows:

| Inducer | Lytic activity (in % for 60 minutes) towards cultures: | | |
| --- | --- | --- | --- |
| | St.aureus | Bac.subtilis | Sacch.cerevisiae |
| Sacch.cerevisiae | 45 | 73 | 46 |

The lytic enzyme is isolated as described in Example 1.

EXAMPLE 7

Czapek nutrient medium is inoculated with the producer agent and all subsequent operations are carried out as described in Example 1.

The cultivation term is five days. The lytic enzyle is isolated as described in Example 1. The obtained lytic enzyme has 30 – 40 per cent lytic activity, towards live cells of St. aureus.

EXAMPLE 8

A nutrient medium containing (in per cent by weight): soya bean flour 0.3, glucose 0.5, $KNO_3$ 0.05, and $K_2HPO_4$ 0.01, is inoculated as in Example 1. A suspension of cells of inducer Staphylococcus aureus in introduced into the nutrient medium before inoculation, as described in Example 1.

The cultivation is carried out with active aeration and stirring for five days.

On the termination of the incubation period, the mycelium is removed from the culture fluid and the lytic activity of the enzyme with respect to Staphylococcus aureus is determined.

| Culture subject to lysis | Lysis time, in hours | Optical density | | Lysis depth, in % for 3.5 hours |
| --- | --- | --- | --- | --- |
| | | initial | final | |
| St. aureus | 3.5 | 15 | 0.25 | 83 |

EXAMPLE 9

Ammonium sulphate is added to the culture fluid obtained in Example 7 to saturate it to 60 per cent. Precipitated protein is washed with acetone, dissolved in a succinate buffer, and then dialyzed.

The dialysate is diluted 1:10 with the buffer solution. Then, to 2 ml of live cells of Chlorella added are 2 ml of the obtained enzyme solution. The optical density is measured with a red filter.

The lytic activity with respect to live cells of chlorella is 29 per cent.

| Culture subject to lysis | Optical density | | | | | Lysis depth, in per cent |
| --- | --- | --- | --- | --- | --- | --- |
| | initial | in 15 min | in 30 min | in 60 min | in 210 min | |
| Chlorella live cells | 12 | 110 | 0.86 | 0.85 | 0.85 | 29 |

What we claim is:

1. A method for preparing a lytic enzyme comprising growing Actinomyces recifensis var. lyticus 2435 in a nutrient medium, containing sources of nitrogen, carbon and mineral salts at a temperature of 25°–28°C for 3–5 days, separating Actinomyces recifensis var. lyticus 2435 from the culture medium and then isolating the lytic enzyme from the culture medium.

2. A method according to claim 1, wherein the process of cultivation is carried out on a nutrient medium having the following composition, in per cent by weight: soya bean flour 0.3, glucose 0.5, $K_2HPO_4$ 0.01, $NH_4NO_3$ 0.1, microelements: $CaCl_2$ 0.11, $MnCl_2$ 0.0012, $MgCl_2$ 0.047, $FeSO_4$ 0.00152, $CuSO_4$ 0.000016, $ZnSO_4$ 0.000017, water to make 100.

3. A method according to claim 2, wherein the cultivation process is carried out at a temperature of 25° – 28°C with aeration for three days.

4. A method according to claim 1, wherein before inoculation, an inducer of synthesis of the lytic enzyme is added to the nutrient medium, said inducer being cell culture selected from the group consisting of Staphylococcus aureus, Micrococcus glutamicus, Bacillus subtilis, Salmonella gallinarum, Saccharomyces cerevisiae.

5. A method according to claim 4, wherein the inducer suspension containing 0.85 – 1 mg of protein per ml, is added to the nutrient medium at a ratio of 1:10 with respect to the nutrient medium.

6. A method according to claim 1, wherein the end product is isolated by saturating the culture fluid to 40 – 60 per cent with ammonium sulphate with subsequent desalting and drying.

7. Lytic enzyme produced by Actinomyces recifensis var. lyticus 2435 produced according to the method of claim 1.

\* \* \* \* \*